(12) United States Patent
Deshmukh et al.

(10) Patent No.: US 10,973,527 B2
(45) Date of Patent: Apr. 13, 2021

(54) LOW PROFILE, SELF-EXPANDING, BLOOD FLOW RESISTING DEVICE

(71) Applicants: Hemant Deshmukh, Mumbai (IN); Krantikumar Rathod, Mumbai (IN)

(72) Inventors: Hemant Deshmukh, Mumbai (IN); Krantikumar Rathod, Mumbai (IN)

( * ) Notice: Subject to any disclaimer, the term of this patent is extended or adjusted under 35 U.S.C. 154(b) by 85 days.

(21) Appl. No.: 16/083,841

(22) PCT Filed: Mar. 9, 2017

(86) PCT No.: PCT/IN2017/050087
§ 371 (c)(1),
(2) Date: Sep. 10, 2018

(87) PCT Pub. No.: WO2017/154025
PCT Pub. Date: Sep. 14, 2017

(65) Prior Publication Data
US 2019/0069903 A1    Mar. 7, 2019

(30) Foreign Application Priority Data
Mar. 11, 2016   (IN) .............................. 201621008656

(51) Int. Cl.
*A61F 2/90*      (2013.01)
*A61B 17/12*     (2006.01)
(Continued)

(52) U.S. Cl.
CPC .... *A61B 17/12172* (2013.01); *A61B 17/1204* (2013.01); *A61B 17/12109* (2013.01); *A61B 17/12177* (2013.01); *A61F 2/90* (2013.01); *A61B 2017/00004* (2013.01); *A61B 2017/00477* (2013.01); *A61B 2017/00867* (2013.01); *A61B 2017/00893* (2013.01);
(Continued)

(58) Field of Classification Search
CPC .......... A61B 17/12172; A61B 17/1204; A61B 17/12109; A61B 17/12177; A61B 2560/0406; A61B 2560/0456; A61B 2560/04; A61F 2/90; A61F 2210/0004; A61F 2210/0014; A61F 2220/0025; A61F 2230/001; A61F 2230/0095; A61F 2250/0039; A61F 2250/0067; A61F 2230/0067
See application file for complete search history.

(56) References Cited

U.S. PATENT DOCUMENTS 5,618,301 A * 4/1997 Hauenstein ...... A61B 17/12036
                                                        623/1.12
5,766,710 A * 6/1998 Turnlund .................. A61F 2/82
                                                        156/148
(Continued)

*Primary Examiner* — Paul B Prebilic
(74) *Attorney, Agent, or Firm* — Ryan Alley IP

(57) ABSTRACT

Low profile, self-expandable, blood flow restrictors include a hollow channel open at axial ends to allow blood flow through the restrictor installed in a blood vessel. The channel may include a mesh and have a narrowing, or sandglass, profile to reduce blood flow. The sandglass shape is in a central portion of the channel and may be surrounded by a blocking coating impermeable to blood flow or a suture that dissolves over time. The mesh may be formed of a memory alloy. Restrictors include a retrieval connector at an end that is permeable to blood flow and permits attachment for restrictor positioning with a catheter.

27 Claims, 7 Drawing Sheets

(51) Int. Cl.
  *A61F 2/06* (2013.01)
  *A61F 2/07* (2013.01)
  *A61F 2/82* (2013.01)
  *A61F 2/95* (2013.01)
  *A61F 5/00* (2006.01)
  *A61B 17/00* (2006.01)

(52) U.S. Cl.
  CPC ... *A61B 2017/12095* (2013.01); *A61F 5/0013* (2013.01); *A61F 5/0089* (2013.01); *A61F 2002/068* (2013.01); *A61F 2002/072* (2013.01); *A61F 2002/823* (2013.01); *A61F 2002/9528* (2013.01); *A61F 2210/0004* (2013.01); *A61F 2220/0041* (2013.01); *A61F 2230/001* (2013.01); *A61F 2230/0067* (2013.01); *A61F 2230/0071* (2013.01); *A61F 2230/0091* (2013.01); *A61F 2250/0015* (2013.01); *A61F 2250/0039* (2013.01); *A61F 2250/0067* (2013.01)

(56) References Cited

U.S. PATENT DOCUMENTS

| | | | |
|---|---|---|---|
| 10,751,159 B2* | 8/2020 | Janardhan | A61F 2/01 |
| 10,898,698 B1* | 1/2021 | Eigler | A61F 2/90 |
| 2003/0040771 A1* | 2/2003 | Hyodoh | D04C 1/06 |
| | | | 606/200 |
| 2005/0055082 A1* | 3/2005 | Ben Muvhar | A61F 2/915 |
| | | | 623/1.15 |
| 2005/0216076 A1* | 9/2005 | Kveen | A61F 2/91 |
| | | | 623/1.22 |
| 2007/0142906 A1* | 6/2007 | Figulla | A61F 2/2436 |
| | | | 623/2.11 |
| 2008/0275540 A1* | 11/2008 | Wen | A61F 2/2418 |
| | | | 623/1.26 |
| 2010/0056978 A1* | 3/2010 | Machan | A61M 1/3655 |
| | | | 604/9 |
| 2011/0144689 A1* | 6/2011 | Isch | A61B 17/1219 |
| | | | 606/194 |
| 2013/0030521 A1* | 1/2013 | Nitzan | A61B 17/0057 |
| | | | 623/2.13 |
| 2013/0245745 A1* | 9/2013 | Vong | A61F 2/844 |
| | | | 623/1.12 |
| 2014/0058436 A1* | 2/2014 | Rosenbluth | A61F 2/07 |
| | | | 606/200 |
| 2014/0249568 A1* | 9/2014 | Adams | A61F 2/013 |
| | | | 606/200 |
| 2014/0330305 A1* | 11/2014 | Rood | A61F 2/013 |
| | | | 606/200 |
| 2014/0350658 A1* | 11/2014 | Benary | A61F 2/07 |
| | | | 623/1.15 |
| 2015/0073533 A1* | 3/2015 | Kassab | A61F 2/01 |
| | | | 623/1.16 |
| 2015/0119633 A1* | 4/2015 | Haselby | A61B 5/14535 |
| | | | 600/16 |
| 2015/0148731 A1* | 5/2015 | Mcnamara | A61B 17/0057 |
| | | | 604/9 |
| 2015/0282922 A1* | 10/2015 | Hingston | A61L 31/048 |
| | | | 623/23.7 |
| 2020/0375768 A1* | 12/2020 | Eller | A61F 2/90 |

* cited by examiner

LOW PROFILE, SELF-EXPANDING, BLOOD FLOW RESISTING DEVICE

FIELD OF THE INVENTION

This invention relates to the field of biomedical engineering.

Particularly, this invention relates to minimally invasive devices.

Specifically, this invention relates to a low profile, self-expanding, blood flow resisting/restricting/controlling device.

BACKGROUND OF THE INVENTION

Minimally invasive devices relate to stents, occluder devices, pacemakers, and the like. Some minimally invasive devices relate to freeing the flow of blood, while some minimally invasive devices relate to occluding the flow of blood. Stents belong to the family of minimally invasive devices which free the flow of blood in a channel such as a blood vessel in which it is deployed. Occluder devices relate to the family of minimally invasive devices which restrict or prevent the flow of blood at the location where it is deployed.

A stent is a mesh 'tube' inserted into blood vessel/conduit in the body to prevent, or counteract, a disease-induced, localized flow constriction In contrast to the function of a stent, an occluder is a percutaneous, transcatheter, device intended to permanently close all types undesired blood flow as seen in aneurisms, Arterio Venus Fistulae, or excessive bleeding from a blood vessel.

In certain conditions, there may be a need to restrict or govern or modulate or partially occlude the flow of blood.

According to a non-limiting exemplary embodiment, one example relates to controlling blood flow to anatomical parts relating to the digestion system. The small intestine is the part of the gastrointestinal tract following the stomach and followed by the large intestine, and is where much of the digestion and absorption of food takes place. The small intestine is where most chemical digestions takes place. Most of the digestive enzymes that act in the small intestine are secreted by the pancreas and enter the small intestine via the pancreatic duct. In human anatomy, the superior mesenteric artery (SMA) arises from the anterior surface of the abdominal aorta, just inferior to the origin of the celiac trunk, and supplies the intestine from duodenum through two-thirds of the transverse colon, as well as the pancreas. Acute complete occlusion of the SMA almost invariably leads to intestinal ischemia and often has devastating consequences, like small intestine gangrenous changes. Causes of the reduced blood flow in celiac, SMA, and Inferior Mesenteric Artery (IMA) can include changes in the systemic circulation (e.g. low blood pressure) or local factors such as constriction (stenosis) of blood vessels/stenosis or occlusion of the SMA (due to Atherosclerosis or Arteritis) leads to pain, which pain results in 'fear of food', otherwise known as cibophobia. This consequently results in weight loss over a period of time without causing intestinal gangrene. However, this weight loss is undesirable and can have debilitating effects on the patient.

According to this non-limiting exemplary embodiment, there is need for a device, for use in obese patients which can induce mild doses of cibophobia by partially restricting the flow of blood in the SMA (supplying the intestine).

This results in the patient being compelled to reduce his/her food intake due to cibophobia, thereby causing weight reduction.

Prior art designs are bulky and non-retrievable, which may cause complications, especially in obese patient. Since the bulky devices (10F) has device has to be inserted through femoral artery, local grain complications like massive hematoma and femoral artery pseudo-aneurysm are common. Bulky and non-retrievable devices can also cause SMA occlusion or Intimal Hyperplasia. Such bulky devices cannot be inserted through the radial artery at the wrist joint since their sizes are more than 10 F in diameter.

OBJECTS OF THE INVENTION

An object of the invention is to provide a device which controls the flow of blood.

Another object of the invention is to provide a device which restricts the flow of blood.

Yet another object of the invention is to provide a device which modulates the flow of blood.

Still another object of the invention is to provide a device which controls the flow of blood, in a blood vessel.

An additional object of the invention is to provide a device which restricts the flow of blood, in a blood vessel.

Yet an additional object of the invention is to provide a device which modulates the flow of blood, in a blood vessel.

Still an additional object of the invention is to provide a device which restricts the flow of blood, in a blood vessel, without causing bowel gangrene.

SUMMARY OF THE INVENTION

According to this invention, there is provided a low profile, self-expanding, blood flow resisting device comprising:

a tubular channel being a hollow channel with open axial ends configured to allow passage of fluids, said tubular channel being a mesh channel, said tubular channel having a sandglass profile, characterised in that, a pre-defined central portion across an axial orientation of said tubular channel being relatively and substantially narrower in width, said tubular channel being made of a shape memory alloy; and a retrieval mechanism advantageously located at an operative proximal end of said device.

Typically, said mesh is a wire mesh with holes, in said mesh, of predefined dimensions.

In at least one embodiment, said tubular mesh channel is a bare-metal channel.

In at least one other embodiment, said tubular mesh channel is a drug-eluting channel.

In at least another embodiment, said tubular mesh channel is a heparin bonded channel.

In at least yet another embodiment, said tubular mesh channel is a covered channel.

In at least still another embodiment, said tubular mesh channel is a coated channel.

In at least an additional other embodiment, said tubular mesh channel is a biodegradable mesh.

Preferably, metal to (surface area of) artery (in which said device is installed) ratio is at least 15% or lesser.

In at least one embodiment, said convex protrusion is a meshed protrusion.

In at least one other embodiment, said convex protrusion is a wire mesh with holes, in said mesh, of predefined dimensions.

In at least another embodiment, said convex protrusion is a bare-metal channel mesh.

In at least yet another embodiment, said convex protrusion is a drug-eluting channel.

In at least still another embodiment, said convex protrusion is a heparin bonded channel.

In at least an additional other embodiment, said convex protrusion is a covered channel.

In at least yet an additional other embodiment, said convex protrusion is a coated channel.

In at least still an additional other embodiment A blood flow resisting device as claimed in claim 1 wherein, said convex protrusion is a biodegradable mesh.

Typically, said convex protrusion is an annularly defined protrusion, in that, said protrusion annularly lining the interior circumference of said tubular mesh.

Typically, said convex protrusion covers the interior circumference of said tubular mesh.

Typically, said convex protrusion is a relatively denser mesh as compared to said tubular channel mesh in order to disallow blood to settle in through its holes and such that it guides the blood about the convex profile.

Typically, said convex protrusion comprises concentric narrowing.

Alternatively, said convex protrusion comprises eccentric narrowing.

Typically, said retrieval mechanism is a conical mesh.

Typically, said retrieval mechanism is a metal structure culminating in a point, said point extending to hoist a screw with male thread around it.

Typically, said retrieval mechanism is a metal structure culminating in a point, said point extending to hoist a screw with male thread around it, characterised, in that, a retrieving catheter comprising a complementary female threaded portion mates with said female threads in order to couple it for pulling it out of its location in a blood vessel.

Alternatively, said retrieval mechanism is a metal structure culminating in a point, said point extending to hoist a hook/snare, characterised, in that, a retrieving catheter comprising a complementary snare/hook configured to couple with the point hook/snare in order to engage it for pulling it out of its location in a blood vessel.

Typically, said device is a sandglass profile device, characterised, in that, there is a substantially central region with its diameter lesser than the diameter of other portions (top and bottom) of said tubular channel, thereby forming a protrusion which protrusion is in the interior side of said tubular channel.

Typically, said device is a self-expandable/collapsible mesh and retrievable.

Typically, said device is made of a shape memory alloy in order to provide self-expanding and self-collapsing characteristics to said device.

Typically, said device is made of absorbable material.

Alternatively, said tubular mesh walls comprising crests and troughs along a pre-defined length in order to form a beaded design.

Alternatively, said tubular mesh is a helical shaped tubular mesh.

BRIEF DESCRIPTION OF THE ACCOMPANYING DRAWINGS

The invention will now be described in relation to the accompanying drawings, in which.

FIGS. 2a, 2b, 2c, 2d, 2e, and 2f illustrate various embodiments of the blood flow resisting device.

Figure 1A:
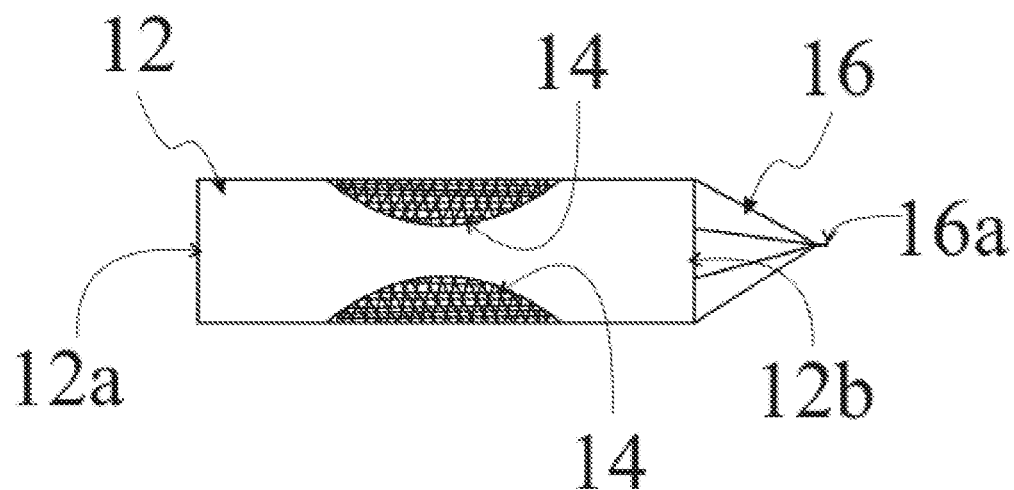
FIG. 1a illustrates a first schematic drawing of the blood flow resisting device.
Figure 3A:
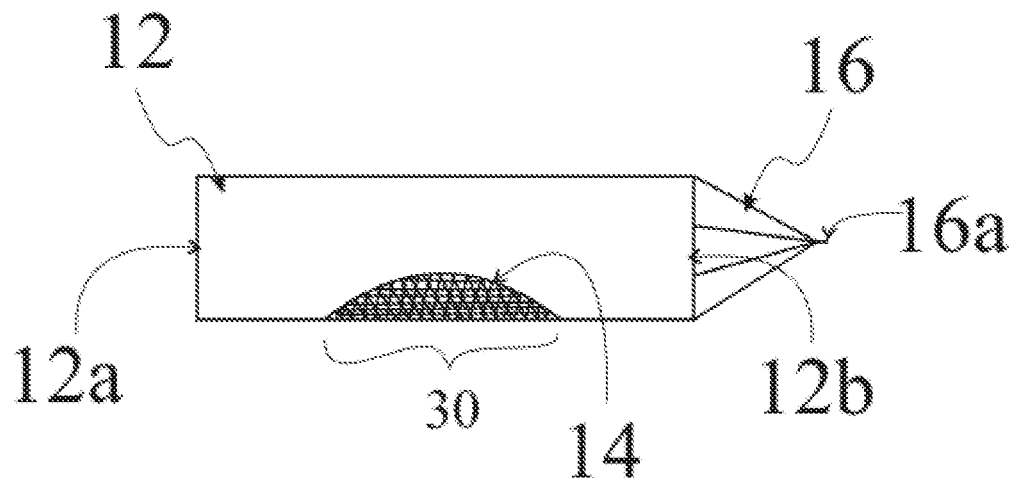

FIG. 3a illustrates an alternative schematic drawing for the device of FIG. 1a.

Figure 1B:
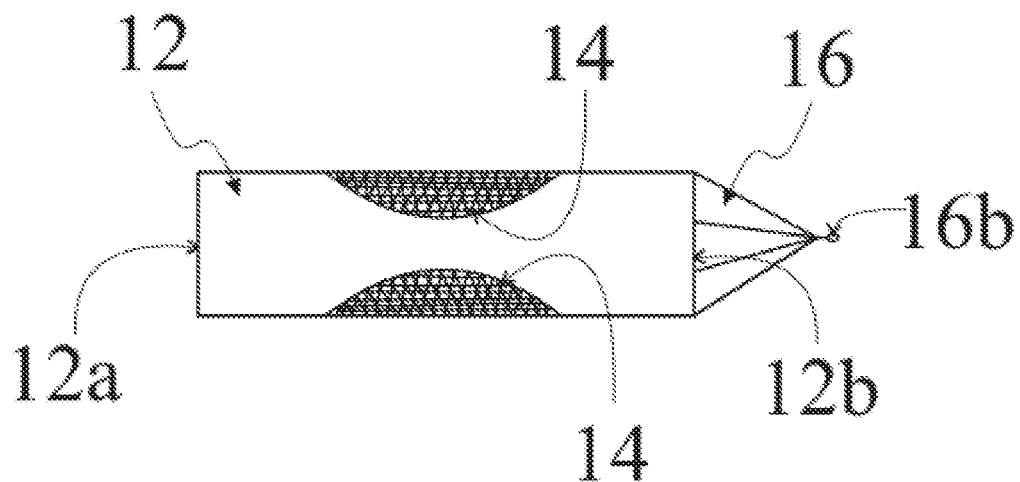
FIG. 1b illustrates a second schematic drawing of the blood flow resisting device.
Figure 3B:
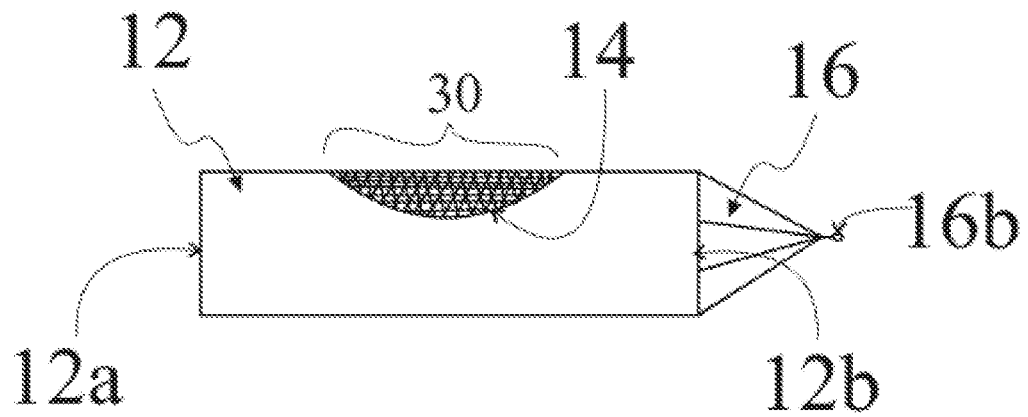

FIG. 3b illustrates an alternative schematic drawing for the device of FIG. 1b.

Figure 2A:
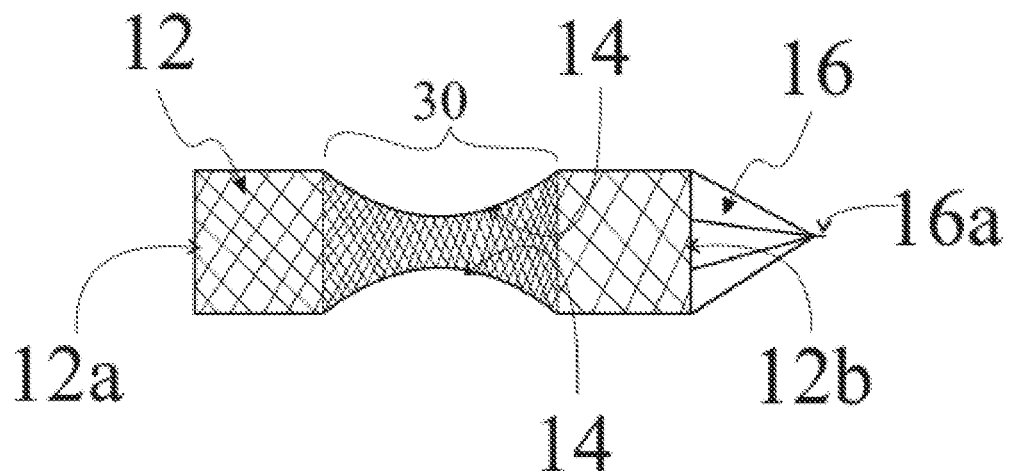
Figure 4A:
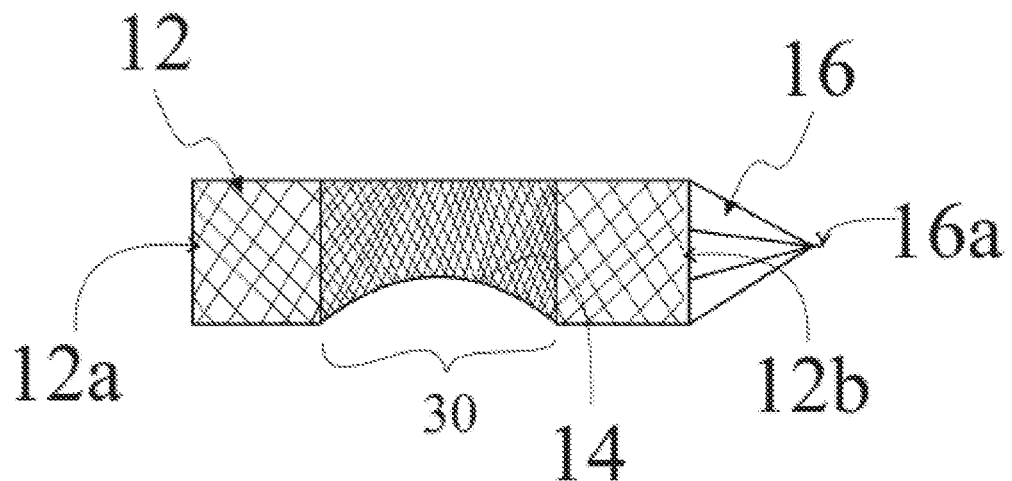

FIG. 4a illustrates an alternative schematic drawing for the device of FIG. 2a.

Figure 2B:
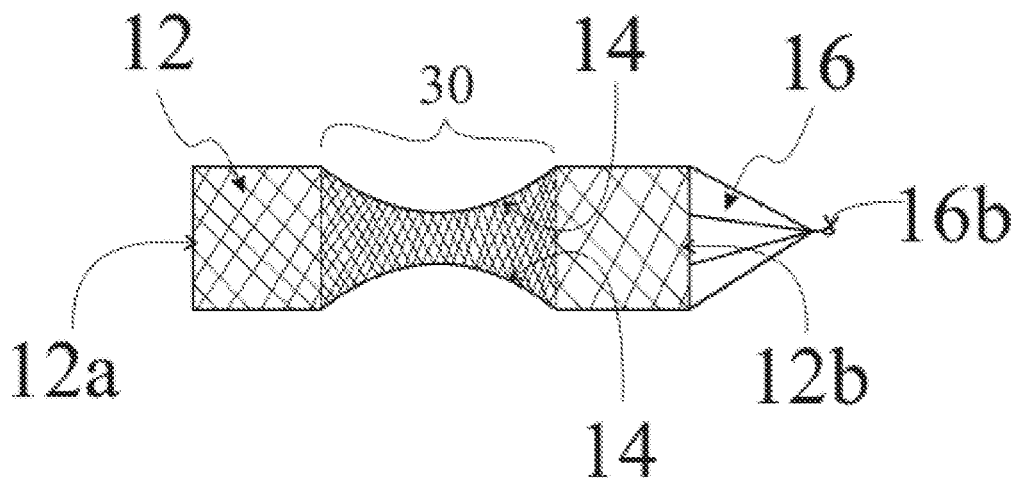
Figure 4B:
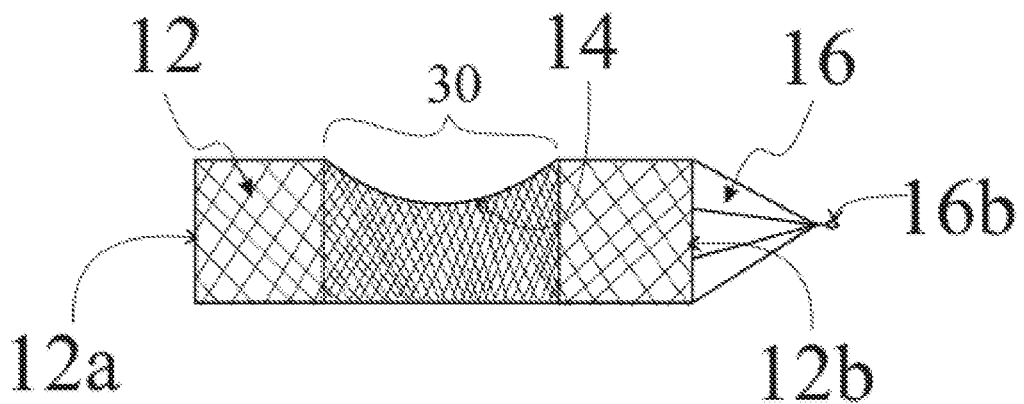

FIG. 4b illustrates an alternative schematic drawing for the device of FIG. 2b.

Figure 5:
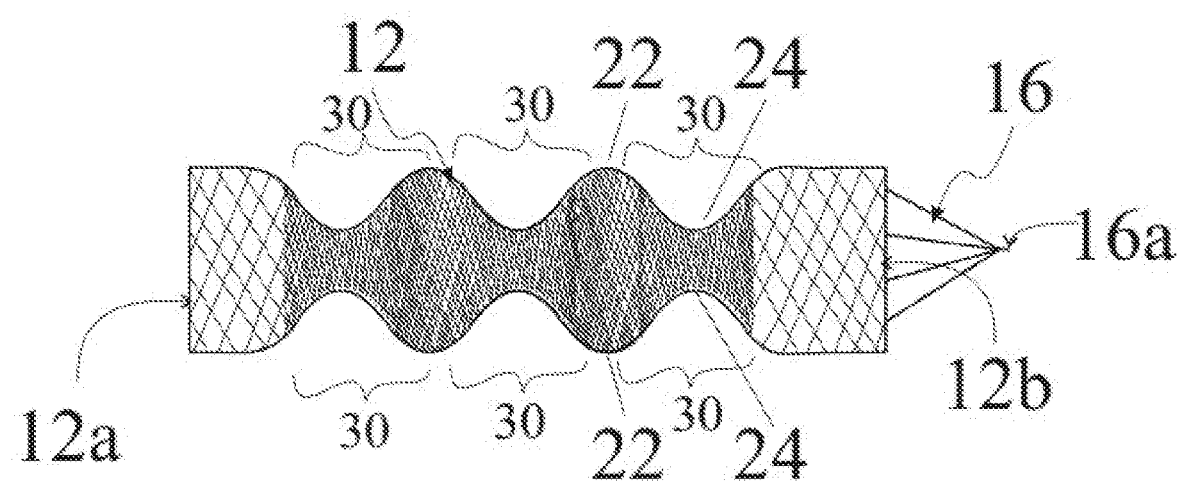

FIG. 5 illustrates a beaded design of the device of this invention.

DETAILED DESCRIPTION OF THE ACCOMPANYING DRAWINGS

According to this invention, there is provided a low profile, self-expanding, blood flow resisting device.

FIGS. 2a, 2b, 2c, 2d, 2e, and 2f illustrate various embodiments of the blood flow resisting device.

FIG. 3a illustrates an alternative schematic drawing for the device of FIG. 1a.

FIG. 3b illustrates an alternative schematic drawing for the device of FIG. 1b.

FIG. 4a illustrates an alternative schematic drawing for the device of FIG. 2a.

FIG. 4b illustrates an alternative schematic drawing for the device of FIG. 2b.

In accordance with an embodiment of this invention, there is provided a tubular channel (12). The tubular channel is a hollow channel with open ends. The tubular channel is adapted to allow passage of fluid, with entry from one open end and exit from the other open end. Typically, the tubular channel is a mesh channel. Typically, the tubular channel is of shape memory alloy such as nitinol. The mesh is a wire mesh with holes, in the mesh, of predefined dimensions. This tubular mesh channel may be a bare-metal channel, a drug-eluting channel, a heparin bonded channel, a covered channel, a coated channel, or the like. The tubular channel may be a biodegradable mesh. Preferably, the metal to (surface area of) artery ratio may be 15% or lesser. One of the open ends is the operative distal end (12a). This is the end which enters a blood vessel first while lodging it or placing it. The other open end is the operative proximal end (12b). This is the end which enters a blood vessel last while lodging it or placing it.

In at least one preferred embodiment of the tubular channel, it has a sandglass profile, characterised in that, a pre-defined central portion (30) across axial orientation of said tubular channel being relatively and substantially narrower in width. This is shown in FIGS. 2a and 2b of the accompanying drawings. The pre-defined central portion, typically, is a tight mesh. Preferably, micron size of this mesh is 10 micron. This mesh is typically tighter or less porous than the rest of the tubular channel.

In at least one embodiment of the tubular channel, there is provided a convex protrusion (14) lining the interior surface of the tubular channel up to a predefined length. The convex protrusion is a meshed protrusion. Further, the convex protrusion is a wire mesh with holes, in the mesh, of predefined dimensions. Further, the convex protrusion is a mesh which may be a bare-metal channel, a drug-eluting channel, a heparin bonded channel, a covered channel, a coated channel, or the like. The convex protrusion is similar to a sandglass profile (when looked at it in a cut-section view). The convex protrusion is an annularly defined protrusion, in that, the protrusion annularly lines the interior circumference of the tubular mesh. Alternatively, the convex protrusion covers the interior circumference, partially (as seen in FIGS. 3a and 3b of the accompanying drawings). The convex protrusion may be a biodegradable mesh. This convex protrusion mesh is a relatively denser mesh as compared to the tubular channel mesh in order to disallow blood to settle in through its holes and such that it guides the blood about the convex profile. The convex protrusion, according to a first embodiment, may have concentric narrowing. The convex protrusion, according to a second alternative embodiment, may have eccentric narrowing. This is shown in FIGS. 1a and 1b of the accompanying drawings.

Figure 2C:
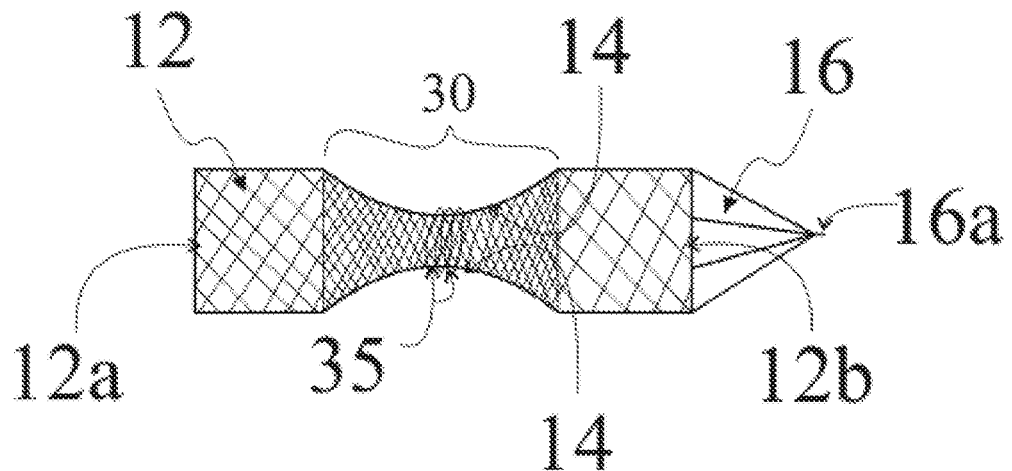
Figure 2D:
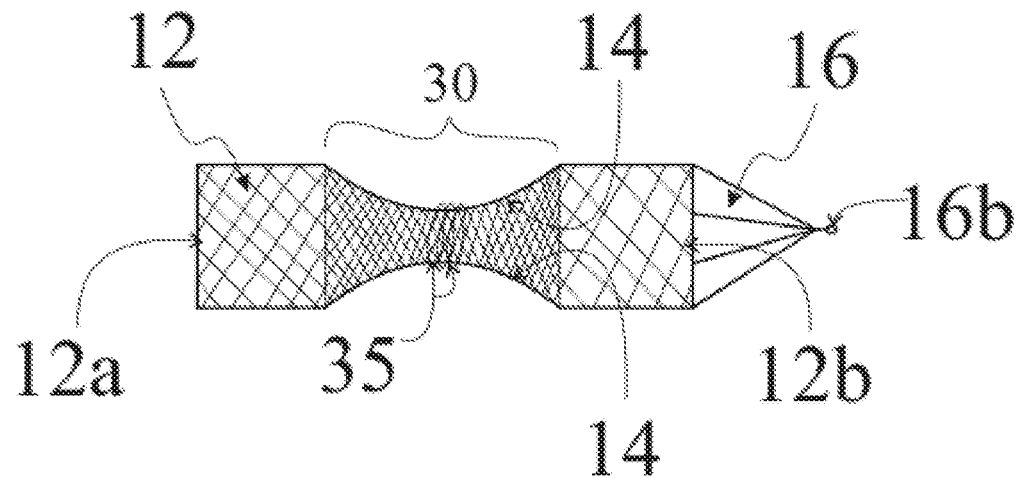

In at least one other embodiment of this invention, tubular channel is bound by an absorbable suture (35) at a substantial central location of the tubular channel. This is shown in FIGS. 2c and 2d of the accompanying drawings. This absorbable suture ensures a sandglass profile for the tubular channel, as long as the suture lasts. The absorbable nature of the suture ensures that the suture dissolves over a time period (preferably, 6 weeks). The shape memory of the tubular channel ensures that the sandglass profile of the tubular channel is temporary, in that, the tubular channel returns to its complete tubular structure after the dissolution of the suture. This ensures that the blood restriction is temporary, the device need not be retrieved.

Figure 2E:
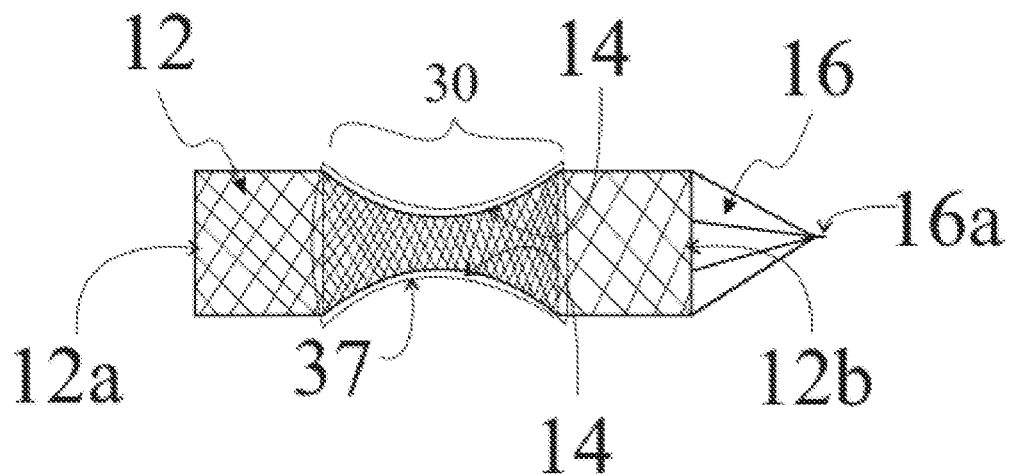
Figure 2F:
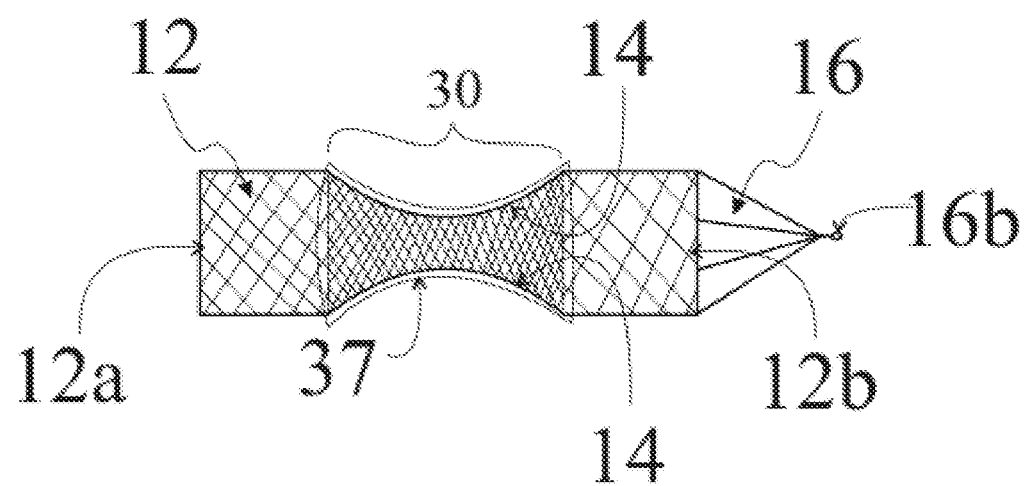

In at least one other embodiment of this invention, there is provided an ePTFE coating (37) about the pre-defined central section (30) which provides the sandglass profile. This ePTFE coating ensures blood does not flow out of the pre-defined central section (30), and is therefore restricted to flow through the constricted channel, thereby achieving its objective of pain and obesity reduction. This is shown in FIGS. 2e and 2f of the accompanying drawings.

In accordance with yet another embodiment of this invention, there is provided a retrieval mechanism (16) advantageously located at the operative proximal end. This retrieval mechanism provides retrievability options in order to remove the device. According to a first embodiment, the retrieving mechanism may be a conical mesh or metal structure culminating in a point. The point may extend to hoist a screw (16a) with male thread around it. In the first embodiment, a retrieving catheter may include a female threaded portion which mates with the female threads in order to couple it for pulling it out of its location in the blood vessel. According to a second alterative embodiment, the point may extend to hoist a hook/snare (16b). In the second embodiment, a retrieving catheter may include a snare/hook which couples with the hook in order to engage it for pulling it out of its location in the blood vessel.

In accordance with an alternative embodiment of this invention, the device is a sandglass profile device. In this profile, there is a substantially central region with its diameter lesser than the diameter the other portions (top and bottom) of the tubular channel Thus a protrusion is formed, which protrusion is in the interior side of the tubular channel. These designs can be seen in FIGS. 2a, 2b, 4a, and 4b of the accompanying drawings.

The device of this invention is a self-expandable/collapsible mesh. This provides flexibility for entry and exit and in the blood vessel. The walls of the tubular channel align with the intima of the blood vessel. The protrusion provides an obstruction for blood flow. It at least one embodiment, the device is made of a shape memory alloy such as Nitinol. This provides self-expanding and self-collapsing characteristics to the device.

Furthermore, in at least one embodiment, the device may be made of absorbable material.

FIG. 5 illustrates a beaded design of the device of this invention. This design comprises crests (22) and troughs (24) which define the beaded design.

Further designs within the scope of this invention comprise helical shape, helix shape, and the like.

According to one non-limiting exemplary embodiment of the use of the device of this invention, the device may be deployed in the SMA through the femoral or radial artery access.

In at least one embodiment, blood flow is reduced by 50%-70%, thereby reducing the flow of blood to the stomach and intestine by at least 50%, and thereby inducing cibophobia, which in turn, induces reduction of body weight.

The technical advancement of the device of this invention lies in its ability to provide blood restricting features with a biocompatible, low profile (6F), and easy retrieving design The INVENTIVE STEP of this invention lies in providing a self-expanding, low profile, blood flow restricting device whose aim is obesity reduction in a patient. The device is made of a shape memory alloy such that in at least one embodiment, it stops it blood restriction function, and retrieval of the device is not required. Further, the device is provided with retrieval mechanisms, advantageously provided, such that the device may be retrieved further to its function of blood flow restriction and further to its objective of obesity reduction.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude or rule out the presence or addition of one or more other features, integers, steps, operations, elements, components, and/or groups thereof.

In an embodiment of the invention, the one or more parts or components of the system of the present invention may be connected and fixed, or may be detachable and re-attachable. Detachable component can be attached or fixed with one or more of other components using mechanisms such as but not limited to screw threads, twist and lock mechanism, magnetic locking, vacuum induced locking, friction fit, snap fit, or any combination thereof.

In an embodiment of the invention, the material used for construction or fabrication of one or more components of the system of the present invention may be any material suitable for performing the function as required for and by one or more component of the system, and may include but is not limited to a metal, a metal alloy, a polymer, rubber, glass, minerals, gem stones, fibre, ceramic, PTFE, ePTFE, or any combination thereof.

While this detailed description has disclosed certain specific embodiments of the present invention for illustrative purposes, various modifications will be apparent to those skilled in the art which do not constitute departures from the spirit and scope of the invention as defined in the following claims, and it is to be distinctly understood that the foregoing descriptive matter is to be interpreted merely as illustrative of the invention and not as a limitation.

We claim:

1. A low profile, self-expandable, blood flow resisting device comprising:

a tubular, hollow channel with open axial ends configured to allow passage of fluids, wherein the tubular channel has a sandglass profile such that a central portion of the tubular channel is relatively narrower in width, and wherein the tubular channel is made of a shape memory alloy mesh; and an open retrieval connector joined around one of the open axial ends to allow passage of the fluids through the connector and to allow retrieval of the device, wherein the open retrieval connector is a conical mesh.

2. A low profile, self-expandable, blood flow resisting device as claimed in claim 1, wherein the central portion is convex in terms of its external profile.

3. A low profile, self-expandable, blood flow resisting device as claimed in claim 1, wherein the mesh is a wire mesh with holes.

4. A low profile, self-expandable, blood flow resisting device as claimed in claim 1, wherein the tubular channel is a bare-metal channel.

5. A low profile, self-expandable, blood flow resisting device as claimed in claim 1, wherein the tubular channel is a drug-eluting channel.

6. A low profile, self-expandable, blood flow resisting device as claimed in claim 1, wherein the tubular channel is a heparin bonded channel.

7. A low profile, self-expandable, blood flow resisting device as claimed in claim 1, wherein the tubular channel is a covered channel.

8. A low profile, self-expandable, blood flow resisting device as claimed in claim 1, wherein the tubular channel is a coated channel.

9. A low profile, self-expandable, blood flow resisting device as claimed in claim 1, wherein the tubular channel is biodegradable.

10. A low profile, self-expandable, blood flow resisting device as claimed in claim 1, wherein the device is sized such that a ratio of surface area of metal of the device to surface area of an inner artery surface in along which the device is installable is 15% or less.

11. A low profile, self-expandable, blood flow resisting device, comprising:
a tubular, hollow channel with open axial ends configured to allow passage of fluids, wherein the tubular channel has a sandglass profile such that a central portion of the tubular channel is relatively narrower in width, and wherein the tubular channel is made of a shape memory alloy mesh; and an open retrieval connector joined around one of the open axial ends to allow passage of the fluids through the connector and to allow retrieval of the device, wherein the open retrieval connector is a metal structure culminating in a point extending to a screw.

12. A low profile, self-expandable, blood flow resisting device as claimed in claim 11, wherein the screw is configured to mate with a retrieving catheter having a complementary female threaded portion to couple with the device for pulling the device out of a blood vessel.

13. A low profile, self-expandable, blood flow resisting device as claimed in claim 1, wherein the conical mesh is a metal structure culminating in a point extending to a hook or snare configured to mate with a retrieving catheter having a complementary snare or hook to couple with the device for pulling the device out of a blood vessel.

14. A low profile, self-expandable, blood flow resisting device as claimed in claim 1, wherein a diameter of the central portion is lesser than diameters of all other portions of the tubular channel.

15. A low profile, self-expandable, blood flow resisting device as claimed in claim 1, wherein the mesh is self-expandable and collapsible.

16. A low profile, self-expandable, blood flow resisting device as claimed in claim 1, further comprising:
an absorbable suture material bound to the central portion, wherein the suture is configured to dissolve in a blood vessel, and wherein the central portion is configured to widen upon dissolution of the suture.

17. The low profile, self-expandable, blood flow resisting device as claimed in claim 1, further comprising:
a coating on the central portion to disallow passage of blood out of the device through the central portion.

18. The low profile, self-expandable, blood flow resisting device as claimed in claim 17, wherein the coating is expanded polytetrafluoroethylene.

19. The low profile, self-expandable, blood flow resisting device as claimed in claim 1, wherein the shape memory alloy mesh is tightest and least porous in the central portion.

20. The low profile, self-expandable, blood flow resisting device as claimed in claim 1, wherein the shape memory alloy mesh in the central portion has 10-micron openings.

21. The low profile, self-expandable, blood flow resisting device as claimed in claim 11, wherein the mesh in the central portion has 10-micron openings.

22. The low profile, self-expandable, blood flow resisting device as claimed in claim 1, wherein the device is sized to fit in the radial artery and superior mesenteric artery.

23. The low profile, self-expandable, blood flow resisting device as claimed in claim 1, wherein the device is configured to reduce blood flow by at least 50% through the device installed in an artery.

24. A blood flow restrictor for use in the superior mesenteric artery, the restrictor comprising:
a tube with open axial ends configured to allow blood flow through the restrictor when installed in the artery, wherein the tube includes a central portion where a flow path inside the tube narrows to a width less than the open axial ends, wherein the central portion of the tube includes a mesh;

an open retrieval connector joined around one of the open axial ends to allow blood flow through the connector and to allow retrieval of the device; and a coating on the central portion to disallow passage of blood out of the device through the central portion.

25. The restrictor of claim 24, wherein the device is configured to reduce blood flow by at least 50% through the artery.

26. The restrictor of claim 25, wherein the flowpath in the central portion narrows and expands along a curve extending axially across the central portion.

27. The restrictor of claim 24, wherein the coating is expanded polytetrafluoroethylene.

* * * * *